United States Patent [19]

Endou et al.

[11] Patent Number: 4,853,638
[45] Date of Patent: Aug. 1, 1989

[54] WATER QUALITY CONTROL METHOD, AND METHOD AND APPARATUS FOR MEASURING ELECTRICAL CONDUCTIVITY USED IN THE WATER QUALITY CONTROL

[75] Inventors: Masao Endou, Hitachi; Yamato Asakura, Katsuta; Atsushi Watanabe, Hitachi; Masaharu Sakagami, Katsuta; Shunsuke Uchida; Makoto Nagase, both of Hitachi; Tsutomu Baba, Katsuta; Katsumi Ohsumi, Hitachi, all of Japan

[73] Assignee: Hitachi, Ltd., Tokyo, Japan

[21] Appl. No.: 141,424

[22] Filed: Jan. 7, 1988

[30] Foreign Application Priority Data

Jan. 9, 1987 [JP] Japan .................................... 62-1651
May 13, 1987 [JP] Japan ............................... 62-114660
Sep. 7, 1987 [JP] Japan ............................... 62-221916

[51] Int. Cl.$^4$ ...................... G01N 27/06; G01N 27/02
[52] U.S. Cl. .................................... 324/441; 324/444; 324/439; 324/57 R; 204/408
[58] Field of Search ..................... 324/57 R, 439, 441, 324/442, 444, 446, 450, 71.2, 65 CR; 204/1 T, 404, 406, 408; 364/497

[56] References Cited

U.S. PATENT DOCUMENTS

| | | | |
|---|---|---|---|
| 4,176,031 | 11/1979 | Rosenblum | 204/408 |
| 4,204,259 | 5/1980 | Yabe | 364/497 |
| 4,238,298 | 12/1980 | Tsuru et al. | 324/57 R X |
| 4,445,091 | 4/1984 | Küsebauch et al. | 324/439 X |
| 4,626,338 | 12/1986 | Kondo et al. | 204/408 X |
| 4,682,113 | 7/1987 | Barben, II | 324/441 |

FOREIGN PATENT DOCUMENTS 59-60293 6/1984 Japan .

Primary Examiner—Reinhrd J. Eisenzopf
Assistant Examiner—Jack B. Harvey
Attorney, Agent, or Firm—Antonelli, Terry & Wands

[57] ABSTRACT

Electric conductivities of an aqueous solution under measurement are measured at two or more different temperatures in a range To to Tn, and a relationship between the electrical conductivity and the temperatures is obtained. A solute substance in the aqueous solution is determined by applying this relationship against a known temperature and electrical conductivity relationship of an individual substance. A concentration of the determined substance is estimated by applying the electrical conductivity at the lowest temperature To to a known relationship between an electrical conductivity and a concentration at the same temperature To with respect to an individual substance.

15 Claims, 19 Drawing Sheets

FIG. 1
FIG. 2
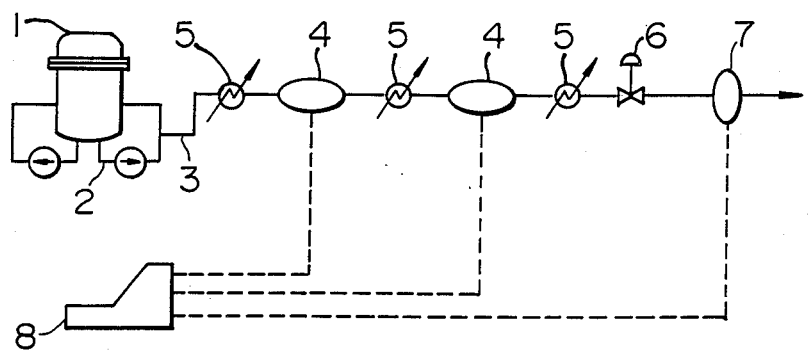
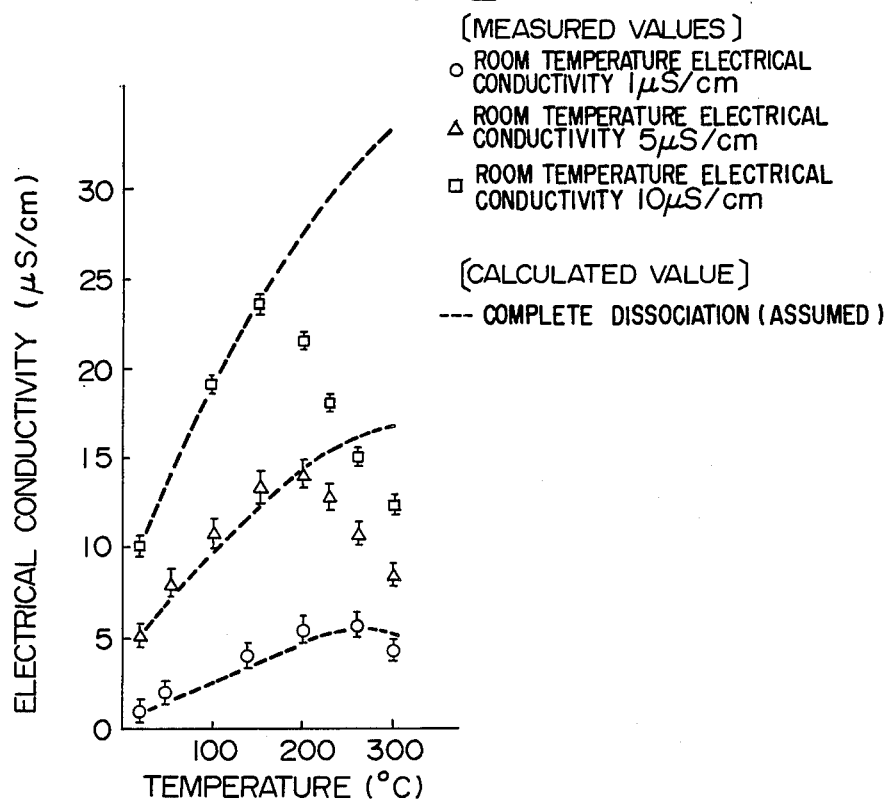

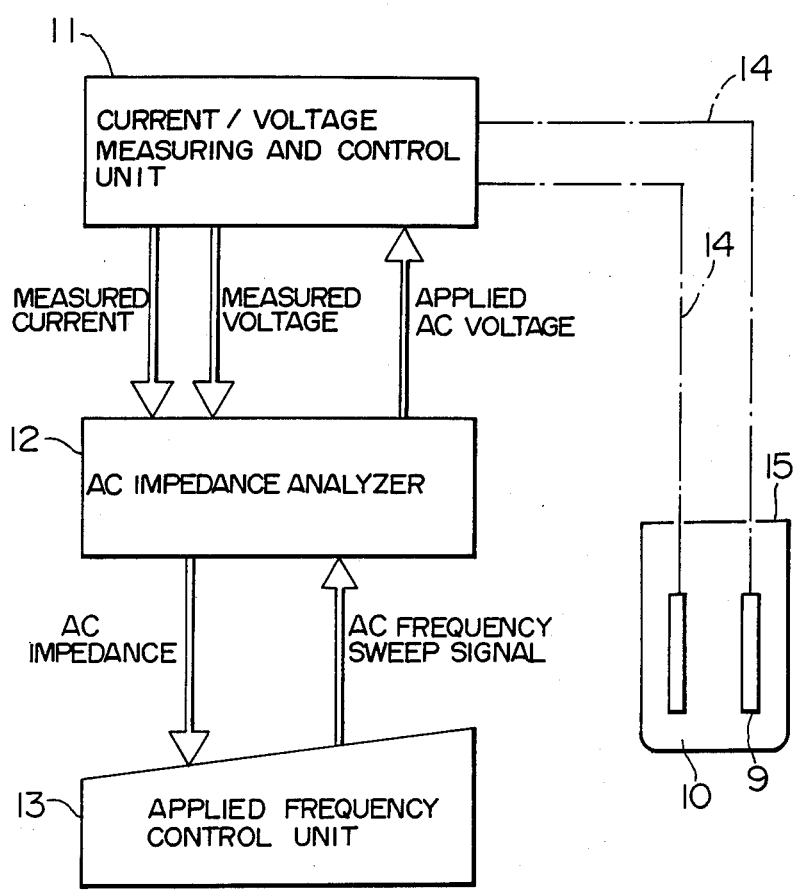

FIG. 9

| STEP | 1 | 2 | 3 |
|---|---|---|---|
| METHOD | SWEEP THE FREQUENCY FROM HIGHER FREQUENCY TO LOWER FREQUENCY | SWEEPING IS STOPPED AT TIME POINT AT WHICH MAXIMUM VALUE OF $-Im[Z]$ IS CONFIRMED | LIQUID RESISTANCE (Rs) AT $\omega \to \infty$ IS ASSUMED FROM AN OBJECT VALUE (SEMICIRCLE) OF LOCUS |
| MEASURED RESULTS | SWEEPING DIRECTION, $-Im[Z]$ vs $Re[Z]$ | $-Im[Z]$ vs $Re[Z]$ | MAX VALUE OF $-Im[Z]$, Rs, $-Im[Z]$ vs $Re[Z]$ |

WATER QUALITY CONTROL METHOD, AND METHOD AND APPARATUS FOR MEASURING ELECTRICAL CONDUCTIVITY USED IN THE WATER QUALITY CONTROL

BACKGROUND OF THE INVENTION

The present invention relates to a water quality control method, and a method and apparatus for measuring an electrical conductivity used in the water quality control. In particular, the present invention relates to water quality control of high temperature water in atomic and thermal power plants, detection of the corrosion rate of a metallic structural member disposed in the aqueous solution in the plants, and to a method and apparatus for measuring electrical conductivity used in the detection of the corrosion rate.

Minute amount of impurities contained in high temperature water affect the corrosion of an analytical metallic material. Accordingly in atomic and thermal power plants, the high temperature water is sampled, and after cooling down and reducing the pressure, electrical conductivity is continuously monitored at room temperature to achieve the water quality control so that the measured value of the room temperature electrical conductivity does not exceed a tolerance value. Specifically, in the prior art, a room temperature electrical conductivity measuring method has been applied for the purpose of continuous monitoring of a corrosive environment and continuous monitoring of inclusion of impurities. Such a water quality control method using the room temperature electrical conductivity measuring apparatus is proposed in Japanese Patent Laid-Open Publication No. 59-60293 (1984).

However, in the method mentioned above, it is difficult to accurately evaluate the high temperature electrical conductivity at corrosive environment temperatures based on the measured values at room temperature because the dissociation of the water per se or the dissociation of the impurities, and the mobility of ions have respectively different temperature dependencies. As a result, in the prior art high temperature water quality control method using the room temperature electrical conductivity, the setting of a standard value for the water quality control is empirical, and the setting of a generally applicable and rational standard value is difficult. Furthermore, even when the room temperature electrical conductivity is the same, since the effect on the corrosion rate in high temperature water differs significantly depending on the chemical form of contained impurities, a problem is involved in that the setting of the standard value for the control of the room temperature electrical conductivity becomes more severe than needed.

Additionally, in the prior art method, the analyzing operation in the analysis of a chemical form of impurities is conducted on the off-line basis, and thus, the analyzing time becomes long. Consequently, it is difficult to detect rapidly formed impurity substances when the water quality is changed abruptly. In particular, it is difficult to detect Cl ion which accelerates the corrosion in high temperature water peculiarly, and to diagnose the cause of the abnormalities.

SUMMARY OF THE INVENTION

An object of the present invention is to realize the rational water quality control in place of the prior art water quality control which uses the room temperature electrical conductivity as an indicator, wherein the high temperature electrical conductivity at a corrosive environment temperature and the temperature dependency of the electrical conductivity in a temperature range from the corrosive environment temperature to the room temperature are used as indicators, and the influence of the chemical form of impurities on the corrosion in relatively high temperature water is taken into consideration.

In one aspect of a method of water quality control in accordance with the present invention, the method comprises the steps of:

(a) measuring electrical conductivities of an aqueous solution under measurement at two or more different temperatures in a range of To to Tn, and obtaining a relationship between the electrical conductivity and the temperature;

(b) determining a solute substance in the aqueous solution under measurement by applying the relationship obtained in the step (a) to a relationship between a temperature and an electrical conductivity of an individual substance obtained beforehand, and (c) estimating a concentration of the determined substance by applying the electrical conductivity at a lowest temperature To among the measurement temperatures in the step (a) to a relationship between an electrical conductivity and a concentration at the same temperature To in an individual substance obtained beforehand.

In another aspect of a method of water quality control in accordance with the present invention, the method comprises the steps of:

(A) immersing at least a pair of electrodes in an aqueous solution under measurement in order to obtain a relationship between an electrical conductivity and a temperature by measuring electrical conductivities at least at two different temperatures in a range of To to Tn with respect to the aqueous solution under measurement, and measuring complex AC impedances of the aqueous solution between the pair of electrodes at each of the temperatures by applying an AC voltage between the pair of electrodes while varying a frequency of the AC voltage;

(B) obtaining a liquid resistance of the aqueous solution under measurement at each of the measurement temperatures from a frequency response of each of the complex AC impedances;

(C) obtaining an electrical conductivity at each of the measurement temperatures in the range of To to Tn from the liquid resistance;

(D) deciding a corrosion rate of a metallic structural member in contact with the aqueous solution by applying a relationship between a highest temperature in the measurement temperatures in the range of To to Tn and the electrical conductivity to a relationship between an electrical conductivity and a corrosion rate of an individual substance obtained beforehand;

(E) determining a solute substance in the aqueous solution under measurement by applying the relationship between the measurement temperature in the temperature range of To to Tn and the electrical conductivity to a relationship between a temperature and an electrical conductivity of an individual substance obtained beforehand; and (F) with respect to the determined substance, estimating a concentration of the substance by applying a part of the relationship obtained in the step (C), that is, the relationship between the temperature and the electrical conductivity at a lowest temperature To, to a relationship between an electrical conductivity and a concentration at the same temperature To with respect to an individual substance obtained beforehand.

The invention was made based on the following new findings by the inventors of the present application.

(1) Even when a solute substance is a strong electrolyte, it becomes substantially difficult to dissociate completely in water at a relatively higher temperature than a room temperature. In other words, in the high temperature water, the concentration of a molecular solute substance which does not dissociate to ions can not be neglected with respect to a concentration of an ionized solute substance.

(2) There is a significant correlation between a high temperature electrical conductivity in an incomplete dissociating condition and a corrosion rate in high temperature water, and the corrosion rate increases in proportion to ½ power of the high temperature electrical conductivity.

(3) The extent of incomplete dissociation changes depending upon the kind of the solute substance, and in particular, a difference between the electric conductivities of different solute substances becomes significant in a high temperature region at 150° C. or higher.

(4) Since the corrosion rate in high temperature water increases not depending upon the chemical form of the impurity but in proportion to ½ power of the high temperature electrical conductivity, it is possible to accurately control the corrosive environment, by using the high temperature electrical conductivity at a corrosive environment temperature as an indicator, based on a common standard value which is not dependent upon the chemical form of the included impurity.

(5) A pattern of electrical conductivity change with temperature exhibits a unique pattern depending upon the kind of solute impurity substances. Thus, the kind of solute impurity substance can be determined by comparing the patterns obtained by measuring the high temperature electrical conductivity at one or a plurality of temperatures in a temperature region higher than the room temperature in which region the solute substance does not dissociate completely. For example, it is possible to decide the presence or absence of Cl ion which is known to have a unique accelerating effect on the corrosion of stainless steel in high temperature water. When the presence of the Cl ion is determined, the concentration of the Cl ion can be determined quantitatively by using an actually measured value of the electrical conductivity in a temperature region, for example, at a room temperature, in which the solute substance is substantially perfectly dissociated. Thus, it is possible to perform the on-line analysis/control of the Cl ion concentration.

BRIEF DESCRIPTION OF THE DRAWINGS

FIG. 1 is a schematic diagram showing a basic arrangement of a BWR type nuclear reactor primary cooling system to which the present invention is applied;

FIG. 2 is a graph showing a comparison between measured values and calculated values of temperature dependency of the electrical conductivity in an aqueous $H_2SO_4$ solution;

FIG. 4 is a schematic diagram showing a basic arrangement of a measuring apparatus used to measure a high temperature electrical conductivity;

FIG. 9 is a diagram illustrating the control performed by the applied frequency control device in FIG. 1 which is unique in the present invention;

DESCRIPTION OF THE PREFERRED EMBODIMENTS

Figure 3:
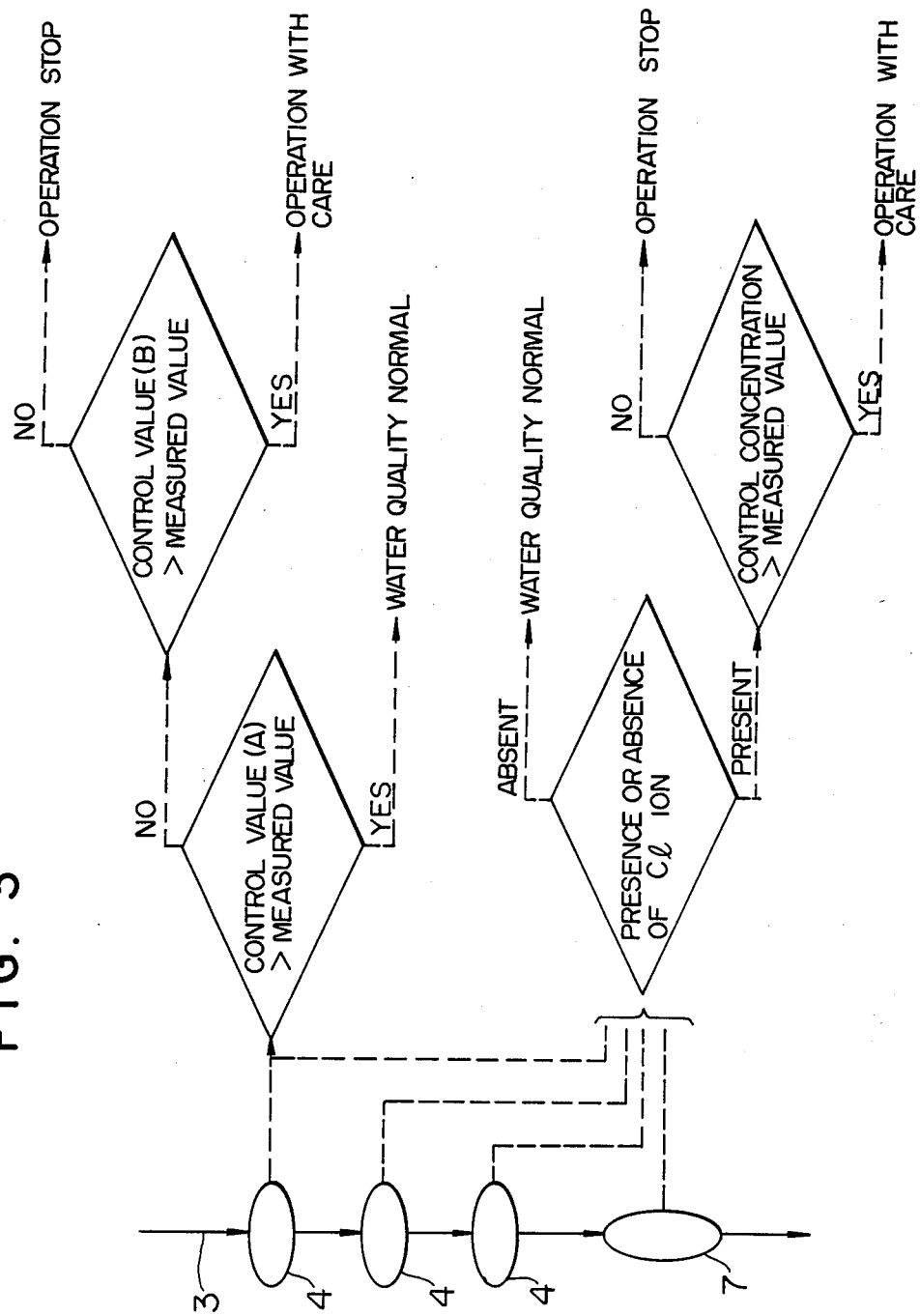
FIG. 3 is a flowchart showing an example of a high temperature water quality control system to which the present invention is applied.

FIG. 1 shows a basic arrangement of components when the present invention is applied to the water quality control of a primary cooling system of a boiling water type nuclear power plant. The components shown in FIG. 1 include a nuclear reactor 1, a coolant recirculation line 2, a reactor water sampling line 3, a high temperature electrical conductivity measuring apparatus 4, a temperature regulator 5, a pressure control valve 6, a room temperature electrical conductivity measuring apparatus 7, and a data analyzer 8. A basic characteristic feature of the arrangement in FIG. 1 resides in that a plurality of electrical conductivity measuring meters for different temperatures are installed on the sampling line of high temperature water, and the water quality is controlled based on a measurement result of the electrical conductivity at each temperature, and the room temperature electrical conductivity measuring apparatus is not necessarily required. Furthermore, the water quality control is possible solely by the high temperature electrical conductivity measuring apparatus which measures at a corrosion environment temperature.

However, as shown in FIG. 2, in the case of an impurity such as $H_2SO_4$ which forms a multivalent anion $(SO_4^{2-})$ by dissociation, the extent of dissociation in high temperature water is lowered remarkably, that is, it dissociates incompletely. As a result, the assumption of complete dissociation can not be applied, and it is difficult to evaluate the amount of included impurity, whether it is large or small, based on the high temperature electrical conductivity. In other words, in order to evaluate the amount of inclusion of impurity, whether the amount is large or small, it is necessary to evaluate by using as an indicator the electrical conductivity measured in a temperature region (a low temperature region equal to or lower than 150° C.) in which the impurity dissociates completely to irons, or the impurity dissociates substantially completely. Moreover, it is known that the Cl ion, among other impurities, accelerates the corrosion peculiarly in high temperature water, and it is necessary to control the concentration of the Cl ion separately from other impurities. For this reason, there is a problem in performing the high temperature water quality control by solely using the high temperature electrical conductivity measuring apparatus in atomic and thermal power plants in which there is the possibility of inclusion of the Cl ion, and it is not practical.

FIG. 3 shows an example of a water quality control system employing the water quality monitoring apparatus shown in FIG. 1. In the system, the high temperature electrical conductivity measured at the corrosion environment temperature is compared with a predetermined control standard value at the corrosion environment temperature, and the effect on the corrosion rate of a structural member which is in contact with high temperature water under measurement is evaluated thereby to decide as to whether the operation of the plant is to be continued or stopped. Furthermore, the changes in the electrical conductivities with temperature measured at a plurality of different temperatures are analyzed, and the presence or absence of Cl ion (included as NaCl) and the amount of inclusion thereof due to a leak of sea-water in a condenser is analyzed. The concentration of the Cl ion is compared with a control reference value with respect to the magnitude thereby to decide as to whether the operation of the plant is to be continued or stopped.

FIG. 4 shows a high temperature electrical conductivity measuring apparatus required in implementing the present invention. The apparatus includes measuring electrodes 9, a liquid sample under measurement 10, a current/voltage measuring and control unit 11, an AC impedance analyzer 12 for measuring an AC impedance between the measuring electrodes, an applied frequency control unit 13, lead lines 14, and a sample container 15. The AC voltage supplied from the analyzer 12 is applied to the measuring electrodes 9 through the current/voltage measuring and control unit 11. The AC current flowing between the measuring electrodes 9 is measured by the current/voltage measuring and control unit 11, and the measured AC current is supplied together with an applied voltage signal to the analyzer 12 thereby to obtain a complex impedance.

Figure 5A:
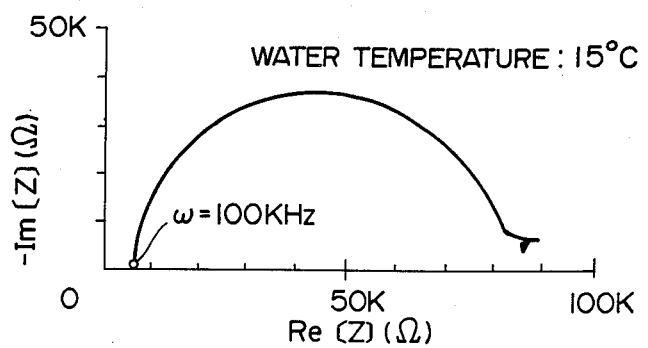
FIGS. 5A and 5B are graphs showing a frequency response of the electrode impedance of platinum electrodes dipped in pure water, plotted on the complex plane in a frequency range from 1 Hz to 100 kHz.
Figure 5B:
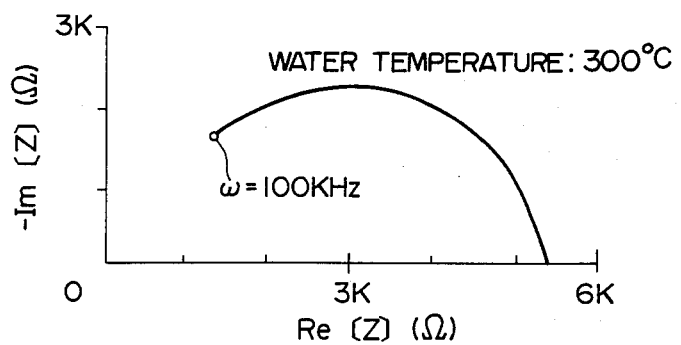
Figure 6:
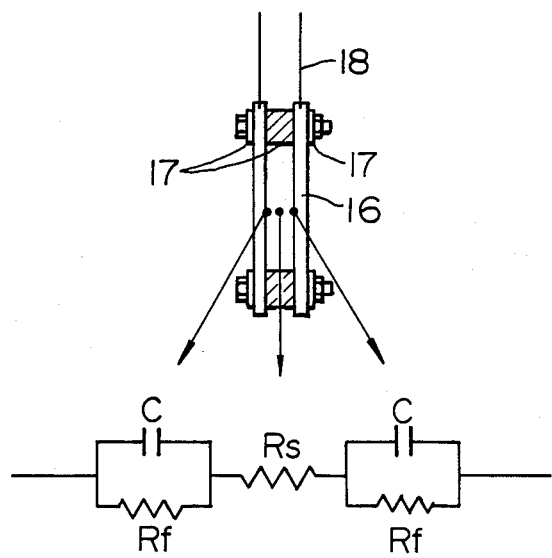
FIG. 6 is a diagram showing an electrical equivalent circuit of the measuring electrode set estimated from the result of analysis of the frequency response of the electrode impedance.

Next, an applied frequency control method unique to the high temperature electrical conductivity measuring apparatus will be described in detail through a concrete application example of the measuring apparatus. FIGS. 5A and 5B show the results of analysis of the AC impedance between the measuring electrodes frequency range from 1 Hz to 100 kHz in which the measuring electrodes include a set of two sheets of platinum electrodes of the same shape and same surface condition fixed with a constant spacing in a range of 2–12 mm. The measuring electrodes are dipped in pure water at respectively 15° C. and 300° C. to measure the AC impedances over a frequency range of 1 Hz–100 K Hz. It was found from the measured results that:

(1) The electrode set can be approximated to an electrical equivalent circuit shown in FIG. 6 in a whole temperature range from room temperature to 300° C.

Figure 7:
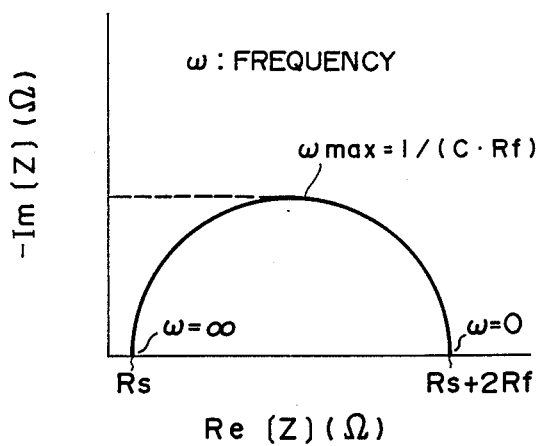
FIG. 7 is a graph showing a locus of the frequency response of a theoretical AC impedance represented by the electrical equivalent circuit of the measuring electrode set.

(2) The obtained locus forms a part of a semicircular locus calculated from the FIG. 6 and shown in FIG. 7.

Figure 8:
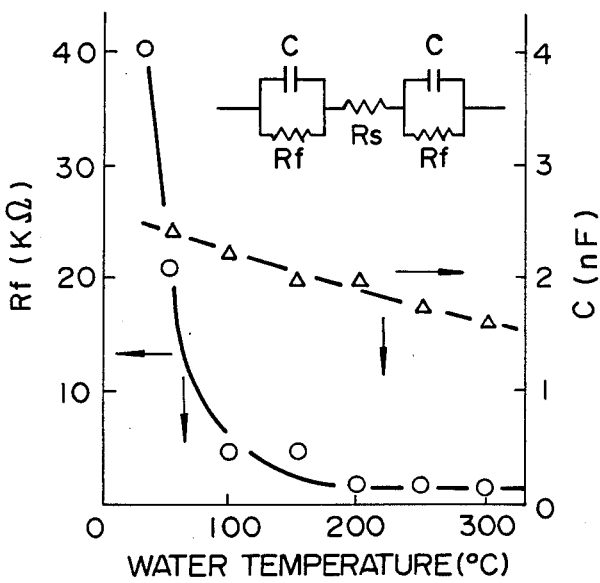
FIG. 8 is a graph showing temperature dependencies of a measuring electrode surface reaction resistance and an electrode capacitance.

(3) However, the changes in the electrode surface reaction resistance Rf and the electrode capacitance C with temperature, which are directly attributable to the electrode surface reaction, are large as shown in FIG. 8, and the frequency required to directly measure the liquid resistance Rs goes higher as the temperature rises.

These results also indicate that the AC signal at a constant frequency of around 10 kHz used in the conventional measurement of the room temperature electrical conductivity is insufficient for the measurement of the liquid resistance Rs at high temperatures. On the other hand, the measurement in a high frequency region equal to 100 kHz or higher imposes the problem in the two points. In other words, there is a significant increase in impedance, i.e., in noises caused by capacitive and inductive components of the lead lines between the measuring electrode set and the measuring apparatus, and furthermore, the frequency dependency of the liquid resistance becomes unnegligible. The inventors paid attention to the fact that the locus of the measured impedance can be approximated on the complex plane by a substantially ideal semicircle or a part of the semicircle, and noticed that the impedance as $\omega = 0$ and at $\omega = \infty$ can be estimated with a sufficient accuracy from a part of the locus by using the applied frequency control unit 13 in FIG. 4. Specifically, FIG. 9 shows a control process performed in the applied frequency control unit 13 in FIG. 4.

First, the frequency is swept from higher to lower frequencies sequentially. A value of the imaginary part of a complex impedance at each frequency is sequentially compared with the measured value of the previous time, and the sweeping of the frequency is stopped at a time point at which it is confirmed that the absolute value of the imaginary part exhibits a maximum value. Supposing that the maximum value is $[Im(Z)]_{max}$, and the value of the real part at this time point is $[Re(Z)]_0$, and a measuring frequency is $\omega_{max}$, a liquid resistance Rs can be obtained from the following formula.

$$Rs = [Re(Z)]_0 - [Im(Z)]_{max}.$$

Figure 10:
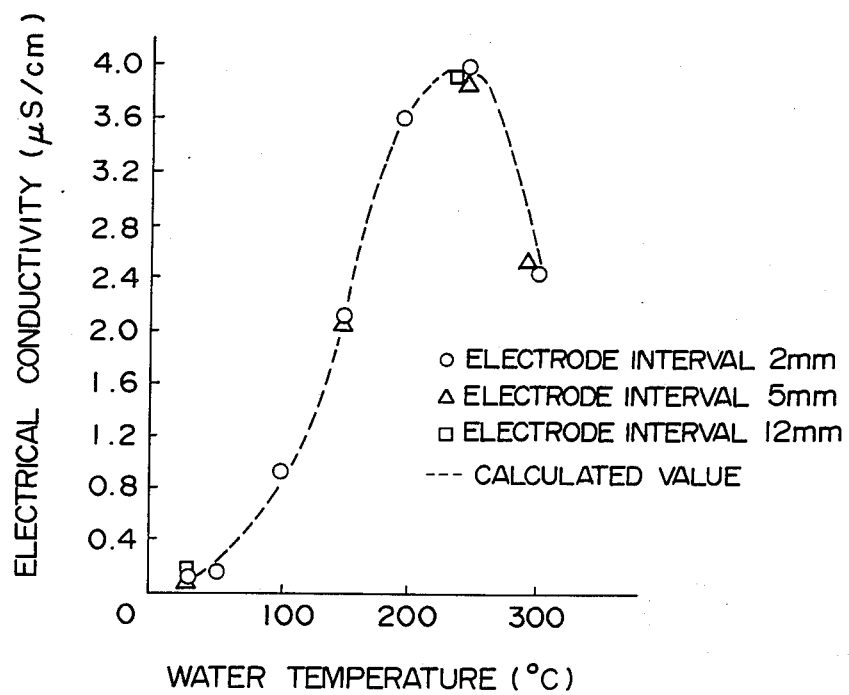
FIG. 10 is a graph showing a comparison between measured results and theoretical calculation results when the present invention is applied to the measurement of electrical conductivity of pure water.

FIG. 10 shows a comparison between a change in the electrical conductivity of pure water with temperature measured according to the method of the present invention and that resulting from the theoretical calculation based on the dissociation of water. Both the measured and theoretical values are coincident with an error of ±5%, and the validity of the above-mentioned measuring technique could be confirmed.

Figure 11:
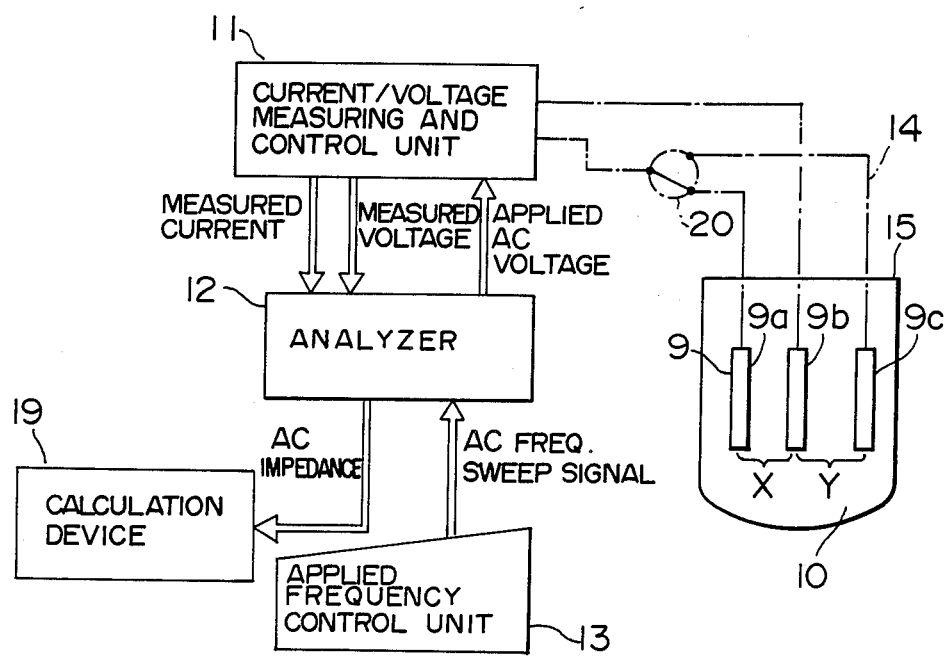
FIG. 11 is a schematic diagram showing an arrangement of another measuring apparatus used in the measurement of the high temperature electrical conductivity.

FIG. 11 shows another high temperature electrical conductivity measuring apparatus required in implementing the present invention. The AC voltage supplied from an analyzer 12 is applied across electrodes 9a and 9b (electrode pair X) through a current/voltage measuring and control unit 11. The AC current flowing between the electrodes 9a and 9b is measured by the current/voltage measuring and control unit 11, and the measured result is supplied together with an applied voltage signal to the analyzer 12 thereby to obtain a complex impedance. Then the electrode 9a is changed over to an electrode 9c by a change-over switch 20, and a complex impedance between the electrodes 9c and 9b (electrode pair Y) is obtained in a similar manner. A calculation device 19 calculates a liquid resistance or an electrical conductivity from the result of measurement of both the complex impedances of the electrode pairs X and Y.

Figure 12:
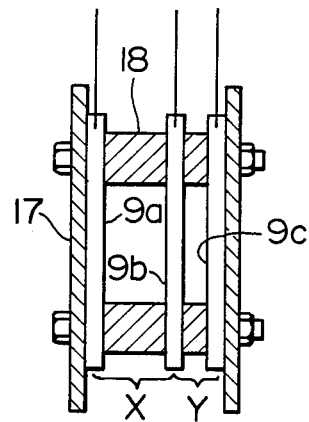
FIG. 12 is a diagram showing a structure of the electrode set.

FIG. 12 shows an electrode structure used in the measuring apparatus in detail. Three sheets of electrode plates 9a, 9b and 9c are arranged in parallel to one another, and the electrode pairs X and Y are arranged so that the electrode surface reaction resistances of both pairs are equal to each other. In order to achieve this, for example, opposite surfaces of the central electrode plate 9b are made electrochemically in substantially the same surface condition to exhibit equivalent electrochemical properties. Also, the surface of each of the electrode plates 9a and 9c positioned at opposite sides, which surface facing the central electrode plate 9b, is formed to exhibit substantially the same electrochemical property. In addition, the intervals in respective electrode pairs X and Y are arranged to be different from each other, that is, the interval between the electrode plates 9a and 9b differs from the interval between the electrode plates 9b and 9c. In this respect, in the present invention, the two pairs of electrode plates may be formed with four sheets of electrode plates (not shown). FIG. 6 shows the electrical equivalent circuit between the electrodes when the electrode pair is dipped in water. FIG. 7 shows the frequency response of the complex impedance plotted on the complex plane. The frequency response is calculated by using the AC impedance between the electrodes obtained from the equivalent circuit of FIG. 6 and by setting numerical values of the AC impedances in the frequency range from zero frequency to substantially infinite frequency. From FIG. 7, a solution resistive component is determined from the measured value in a higher frequency range, and the sum of a surface reaction resistance (Rf) and a solution resistance (Rs) is determined from the measured value in a lower frequency range.

Figure 13:
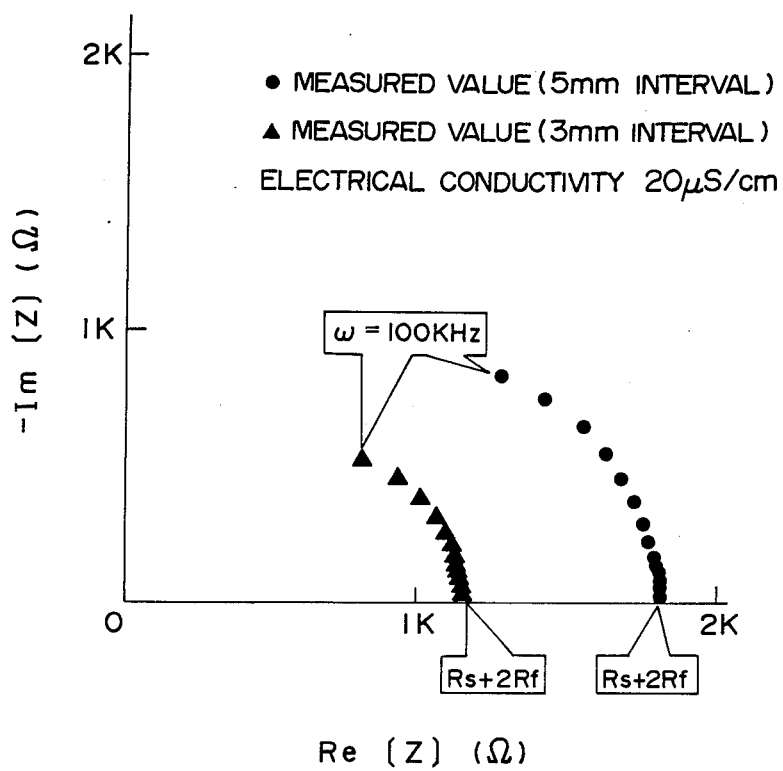
FIG. 13 is a graph showing the results of analysis of a frequency response of the electrode impedance when the electrode set is dipped in a high electrical conductivity liquid.

FIG. 13 shows the result of measurement of the frequency response of impedance when three sheets of platinum plates are used as electrode plates. Each of the platinum plates has a size of 25 mm × 50 mm and a thickness of 1 mm, and the surface condition (ground condition) of the opposite surfaces of each platinum plate is equivalent, and the interval in the electrode pair X is 5 mm and the interval in the electrode pair Y is set to be 3 mm. When the electrical conductivity is equal to 5 μs/cm or larger, even when the AC impedance is measured at the maximum frequency of 100 kHz acceptable in the measurement, the semicircular locus as shown in FIG. 7 can not be obtained. Thus, it is difficult to determine the solution resistive component from the measured values in the higher frequency region with high accuracy. In contrast, the value of 2Rf+Rs can be determined accurately from the measured values in the lower frequency region. Supposing that the value of $2Rf + Rs_1$ between the electrodes having the electrode interval ($L_1$) of 5 mm is $Z_1$, and the value of $2Rf + Rs_2$ between the electrodes having the electrode interval ($L_2$) of 3 mm is $Z_2$, the specific electrical conductivity ($\kappa$) of the liquid is obtained from the following formula.

$$1/\kappa = \{(Z_1) - (Z_2)\}/(L_1 - L_2) = \quad (1)$$
$$\{(Rs_1 + 2Rf) - (Rs_2 + 2Rf)\}/(L_1 - L_2) =$$
$$(Rs_1 - Rs_2)/(L_1 - L_2) \quad (1)$$

Furthermore, in the present invention, when the electrode interval is unknown, the value of $(L_1 - L_2)$ can be estimated as follow. Namely, since a difference between $Z_1$ and $Z_2$ is proportional to a reciprocal number of the electrical conductivity, it is possible to convert to the electrical conductivity by obtaining the value of $(L_1 - L_2)$ (proportional constant of the electrodes) from the measurement of a liquid whose electrical conductivity is known.

In the present invention, the effect of the polarization occurring on the electrode surface which affects the result of measurement adversely can be neglected by applying an AC voltage at a frequency equal to 10 Hz or higher. Thus, the dependency of measured impedance on the current density can be suppressed to a great extent.

Figure 14:
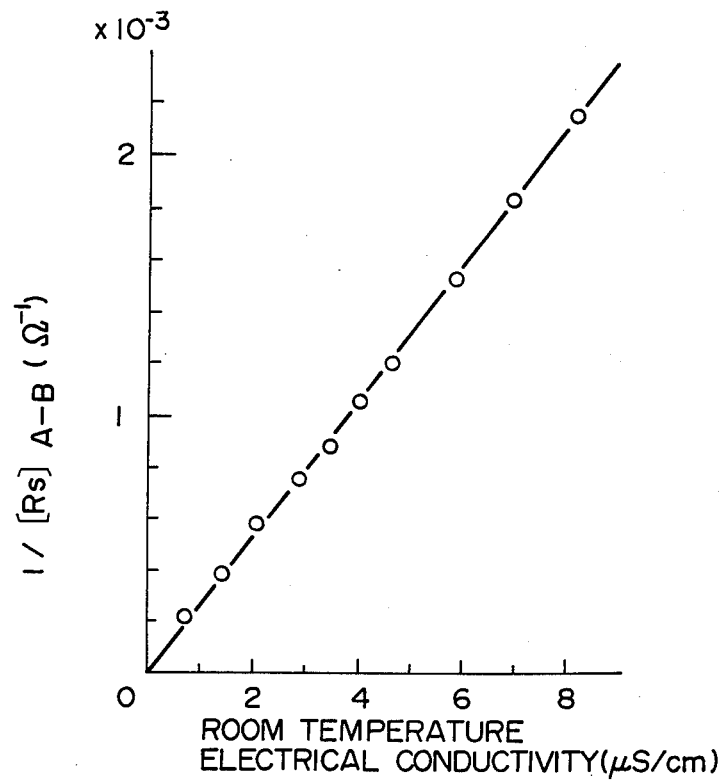
FIG. 14 is a graph showing a correlation between the results of measurement of a liquid resistance at room temperature by a measuring apparatus of the present invention and the results of measurement by an electrical conductivity measuring apparatus available in the market.
Figure 15:
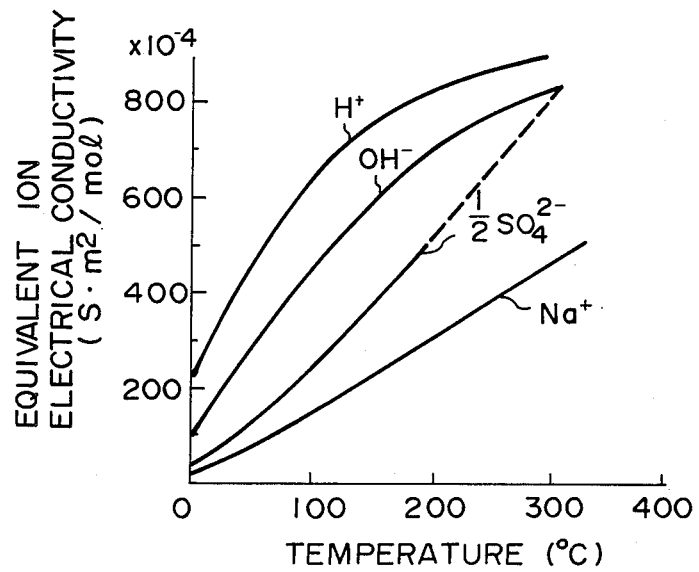
FIG. 15 is a graph showing changes in equivalent ion electrical conductivity with temperature which is used in calculating the high temperature electrical conductivity.
Figure 16:
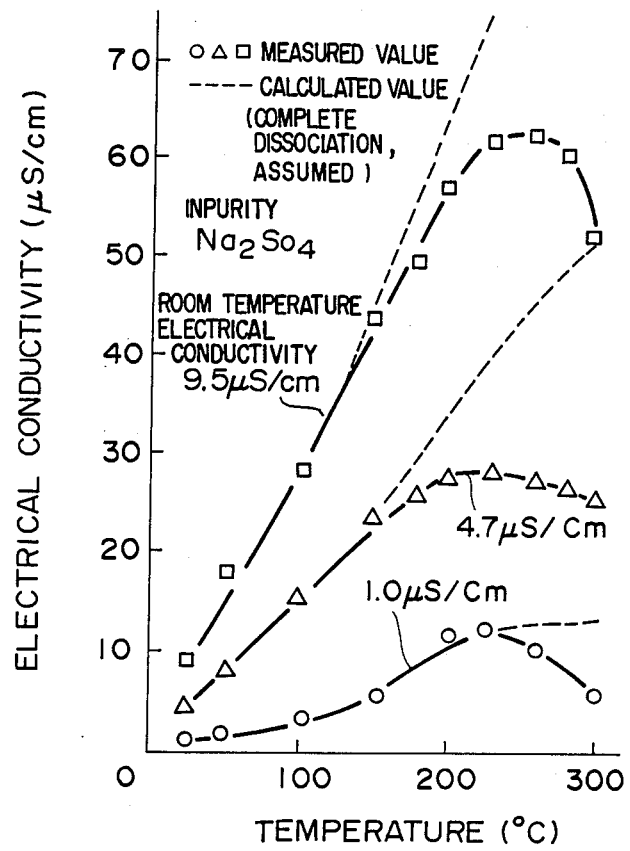
FIG. 16 is a graph showing a comparison between changes in measured value and theoretical calculation value of the electrical conductivity with temperature when $Na_2SO_4$ is dissolved as an impurity.

FIG. 14 shows a correlation between a value of 1/Rs obtained by the method of the present invention and a room temperature electrical conductivity measured by an electrical conductivity measuring apparatus on the market, wherein the room temperature electrical conductivity is changed in a range from 0.8 to 8 ρS/cm. A satisfactory linear relation is recognized between both the values, and the validity of the measuring technique in the present invention was confirmed.

In the embodiment described above, the same voltage is applied to the electrode pairs X and Y, and the frequency of 10 Hz is used as a lowest frequency. However, a low frequency alternating current of a frequency lower than 10 Hz may be used. However, if a load frequency alternating current of a frequency equal to 1 Hz or lower is used, the obtained value of 2Rf+Rs will be changed depending on the current density of a current flowing between the electrodes (Rf is changed depending on the current density). Accordingly, it is necessary to adjust the voltages respectively applied to the electrode pairs X and Y, so that the current densities in the electrode pairs X and Y are equal to each other. Furthermore, in embodiment, the measuring electrode set of a three-electrode structure of fixed type is used. However, similar effects will be obtained by using a measuring electrode set of a two-electrode structure with the electrode interval variable in two stages or more.

In the embodiment, the parallel, flat plate type electrodes are used. However, electrodes of a coaxial cylindrical type having equal lengths in the axial direction and having different radiuses may be used to obtain similar effects.

When a solute impurity (or an impurity solved and held in a solution) dissociates completely also in high temperature water, the high temperature electrical conductivity can be obtained analytically by the following well-known method based on the concentration of the solute impurity. Thus, the high temperature electrical conductivity measuring apparatus described in the foregoing becomes unnecessary. Specifically, as ionic species in reactor water, there exist $H^+$ and $OH^-$ formed by ionization of the water, besides $A^+$ and $B^-$ formed by ionization of an impurity having a schematic chemical form represented by A·B and leaked into the reactor water. Supposing that, the molarity of each ionic species is $C_i$ (mol/m$^3$), and the equivalent ionic electrical conductivity is $\lambda_i$ (S·m$^2$/mol), the electrical conductivity K (S/m) is expressed by the following formula.

$$K = \Sigma C_i \cdot \lambda_i \quad (5)$$

The molarity of each ionic species can obtained by calculation from the following two conditional formulae (6) and (7), if the initial amount of addition is determined. That is, the conditional formula (6) for electrical neutrality of each ionic species in the solution;

$$C_A^+ + C_H^+ = C_B^- + C_{OH}^- \quad (6), \text{ and}$$

the conditional formula (7) for ionization equilibrium;

$$C_H^+ \cdot C_{OH}^- = K \quad (7)$$

Figure 17:
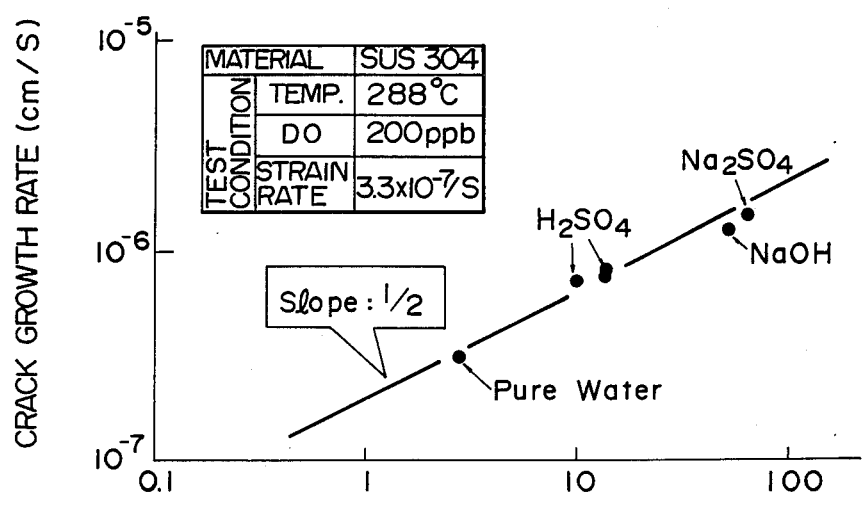
FIG. 17 is a graph showing a correlation between the high temperature electrical conductivity and corrosion rate which forms the basis of the present invention.
Figure 18:
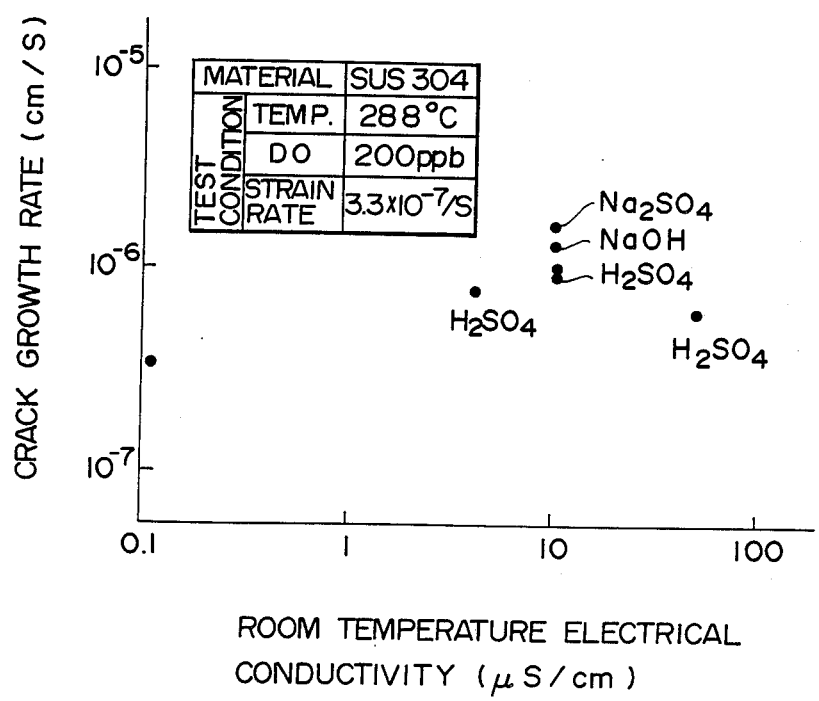
FIG. 18 is a graph showing a correlation between the room temperature electrical conductivity and the corrosion rate known in the art.

(here, K is the ionic product). In molarity can be obtained from the simultaneous formulae (6) and (7). On the other hand, with respect to the equivalent ionic electrical conductivity, the calculated values in the infinite dilution condition as shown in FIG. 17 are reported. FIG. 18 shows a comparison between the calculated values as to $Na_2SO_4$ using the values in FIG. 17 and actually measured values. In the past, $Na_2SO_4$ had been considered to dissociate completely in high temperature water as a strong electrolyte substance. However, it was revealed from the experimental results shown in FIG. 18 that the formula for calculating the electrical conductivity on the premise of complete dissociation is applicable only on the condition that the room temperature electrical conductivity is equal to 1 $\mu$S/cm or smaller and the water temperature is equal to 200° C. or lower, and that when the water temperature is equal to 200° C. or higher, the electrical conductivity exhibits a value which differs considerably from the high temperature electrical conductivity which had been predicted till then from the calculation.

FIG. 17 shows a correlation between the stress corrosion crack growth rate of stainless steel (SUS 304) which has been subject to sensibility treatment and the high temperature electrical conductivity. The correlation shown in FIG. 17, that is, the high temperature electrical conductivity at a corrosive environment temperature measured by using the high temperature electrical conductivity measuring apparatus is applied to the evaluation of the stress corrosion cracking environment. It is confirmed that the stress corrosion crack growth rate is not dependent upon the chemical form of the impurity, but increases in proportion to $\frac{1}{2}$ power of the high temperature electrical conductivity. Accordingly, the degree of influence of the electrical conductivity on the stress corrosion cracking phenomenon can be evaluated quantitatively, and the rational water quality control corresponding to the operation history of the plant can be realized.

Next, for the purpose of comparison, the correlation between the stress corrosion crack growth rate and the room temperature electrical conductivity known in the art is shown in FIG. 18. However, since the correlation is not satisfactory, it is difficult to accurately evaluate the stress corrosion cracking environment based on the room temperature electrical conductivity. For this reason, in order to achieve the control with sufficient margin with respect to the safety, in the case of the water quality control based on the room temperature electrical conductivity, the water quality control standard value must be set more severely than it is necessary.

Figure 19:
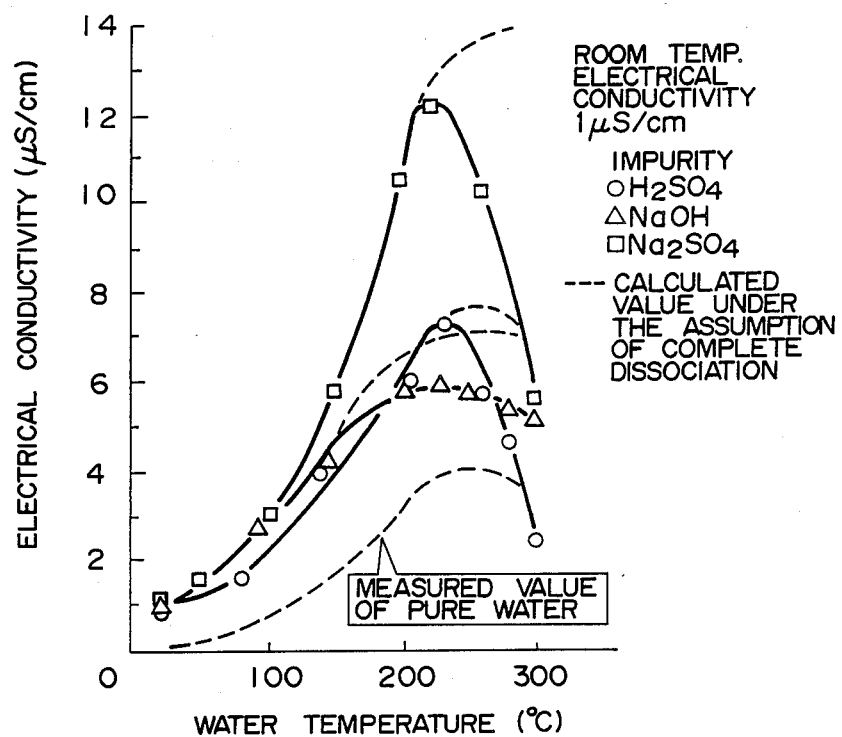
FIGS. 19 and 20 are graphs respectively showing comparisons among three kinds of solute substances of NaOH, $H_2SO_4$ and $Na_2SO_4$ as to patterns of changes in electrical conductivities with temperature when the room temperature electrical conductivities are constant.
Figure 20:
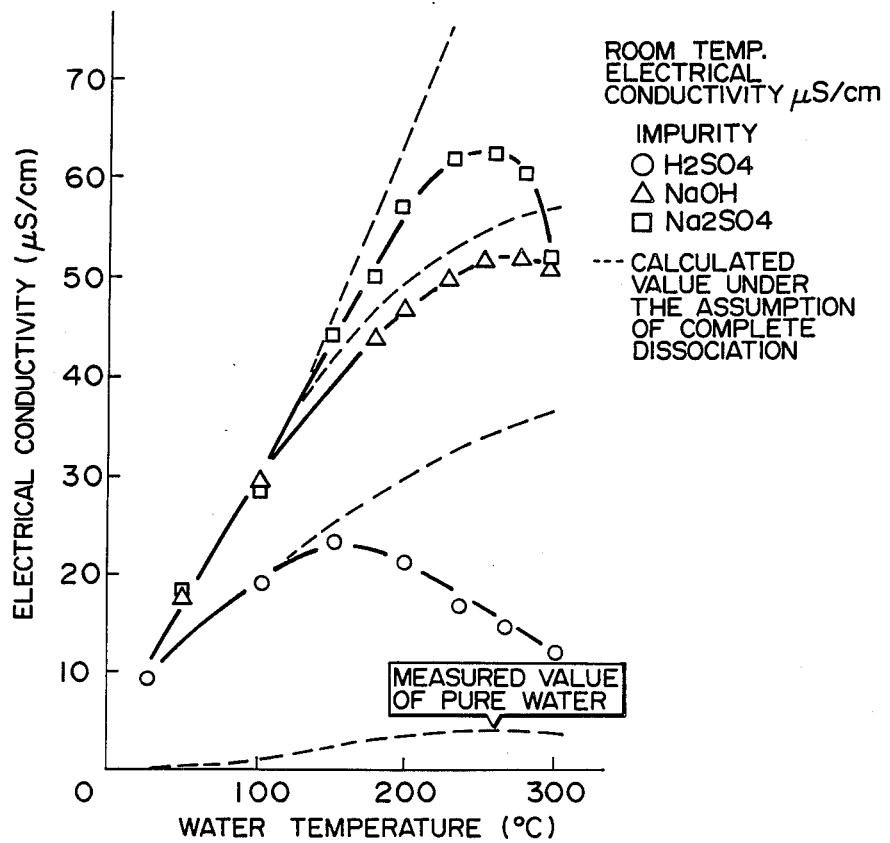

Hereinafter, a method of determination of a solute substance which is unique in the present invention will be described by way of concrete examples showing the application of the method. FIGS. 19 and 20 show the results obtained experimentally as to the correlation between a variation in room temperature electrical conductivity and a variation in high temperature electrical conductivity as to the three kinds of solute impurities; NaOH, $H_2SO_4$ and $Na_2SO_4$. Specifically, a change in electrical conductivity of aqueous solution with temperature is shown for each of the three kinds of impurities in contrast to one another, wherein imitatively, the three kinds of impurities are respectively dissolved in pure water having a room temperature electrical conductivity of 0.1 $\mu$S/cm, and the room temperature electrical conductivity of the solution is adjusted to 1 $\mu$S/cm (in FIG. 19) and 9.5 $\mu$S/cm (in FIG. 20). As will be seen from FIGS. 19 and 20, although the room temperature electrical conductivity is the same, the change in electrical conductivity with temperature exhibits a pattern peculiar to each of the impurities, and in particular, in a temperature range of 150°–250° C., the differences among the solute substances become significant. Accordingly, by measuring an increase in the room temperature electrical conductivity for pure water, and by using the results shown in FIGS. 19 and 20, for example, the amount of increase in the high temperature electrical conductivity at 200° C. is predicted for each of the three kinds of solute impurities; NaOH, $H_2SO_4$ and $Na_2SO_4$. Then, by comparing the predicted results with actually measured values of the increase in the high temperature electrical conductivity, it is possible to determine the kinds of the solute substances contained in the core water. Once the kinds of the solute substances have been determined, it is possible to further analyze the concentrations of the solute substances based on the value of the room temperature electrical conductivity.

EMBODIMENT 2

In the embodiment described above, in predicting the amount of increase in the high temperature electrical conductivity, the actually measured data relating to the change in electrical conductivity with temperature obtained when the room temperature electrical conductivity is made to change for each kind of solute substance is used as it is. However, when the room temperature electrical conductivity is equal to 1 $\mu$S/cm or less and the water temperature is equal to 200° C. or lower, it is possible to obtain the amount of increase in the high temperature electrical conductivity analytically by using the following method known in the art. When the room temperature electrical conductivity of a sample under measurement exceeds 1 $\mu$S/cm, pure water for dilution can be supplied at the upstream side of the electrical conductivity measuring apparatus so that the room temperature electrical conductivity decreases to 1 $\mu$S/cm or less.

EMBODIMENT 3

In the embodiment 2, in order to apply the present invention to the analysis of an aqueous solution having a room temperature electrical conductivity equal to 1 $\mu$S/cm or larger, a dilution device is provided at the upstream side of the high temperature electrical conductivity measuring apparatus. However, when the high temperature electrical conductivity of each kind of solute substance is known, whose room temperature electrical conductivity is close to the room temperature electrical conductivity of an aqueous solution under measurement, it is possible to know the high temperature electric conductivity of the aqueous solution under measurement approximately by the following method. That is, a change in electrical conductivity with temperature when the room temperature electrical conductivity is A $\mu$S/cm (A >1), is obtained experimentally for each of NaOH, H$_2$SO$_4$ and Na$_2$SO$_4$, and the obtained values are expressed respectively as a function of temperature (T) by $f_{NaOH}$ (T), $f_{H_2SO_4}$ (T) and $f_{Na_2SO_4}$ (T). Supposing that the room temperature electrical conductivity C $\mu$S/cm of the aqueous solution under measurement is changed from C $\mu$S/cm to C+$\Delta$C $\mu$S/cm by $\Delta$C $\mu$S/cm, the amounts of change $\Delta f_{NaOH}$ (T$_0$), $\Delta f_{H_2SO_4}$ (T$_0$) and $\Delta f_{Na_2SO_4}$ (T$_0$) of the high temperature electrical conductivity at a temperature T$_0$ can be obtained from the following formulae (8)–(10).

$$\Delta f_{NaOH} (T_0) = \Delta C \times \frac{\{f_{NaOH} (T_0) - f_0 (T_0)\}}{(A - A_0)} \quad (8)$$

$$\Delta f_{H_2SO_4} (T_0) = \Delta C \times \frac{\{f_{H_2SO_4} (T_0) - f_0 (T_0)\}}{(A - A_0)} \quad (9)$$

$$\Delta f_{Na_2SO_4} (T_0) = \Delta C \times \frac{\{f_{Na_2SO_4} (T_0) - f_0 (T_0)\}}{(A - A_0)} \quad (10)$$

where, A$_0$ is a value of the electrical conductivity of pure water at room temperature, and f$_0$(T$_0$) is a value of the electrical conductivity of pure water at a temperature T$_0$. Furthermore, in order to enhance the accuracy of approximation, $\Delta C \simeq (A - A_0)$ is a necessary condition. By comparing the values of $$\Delta f_{NaOH} (T_0), \Delta f_{HSO_4} (T_0), \text{ and } \Delta f_{Na_2SO_4}$$

estimated by the above formulae with actually measured values, it is possible to directly determine a solute substance in an aqueous solution whose electrical conductivity is equal to 1 $\mu$S/cm or larger without deluting the solute substance.

EMBODIMENT 4

In the above embodiments, the object solute substances to be determined are NaOH, H$_2$SO$_4$ and Na$_2$SO$_4$. However, the present invention can be applied by a similar technique to aqueous solutions containing other electrolyte substances.

When the reactor water of a nuclear reactor is the object of measurement, the substances which are highly possible to be included in the reactor water are the following two kinds of substances. One is NaCl included due to leakage of sea water in the condenser, and the other is H$_2$SO$_4$ produced by thermal decomposition of ion exchange resin which flows into a core section from a condensating and desalting device where the ion exchange resin is used.

In order to control the concentration of Cl ion which has a peculiar acceleration effect on the corrosion in high water temperature, the temperature dependency of the electrical conductivity is measured in a range from a corrosive environment temperature to a room temperature. By utilizing the fact that such a temperature dependency exhibits a pattern inherent in a chemical form of the impurity, the chemical form of the impurity, in particular, the presence or absence of Cl ion is decided.

Figure 21:
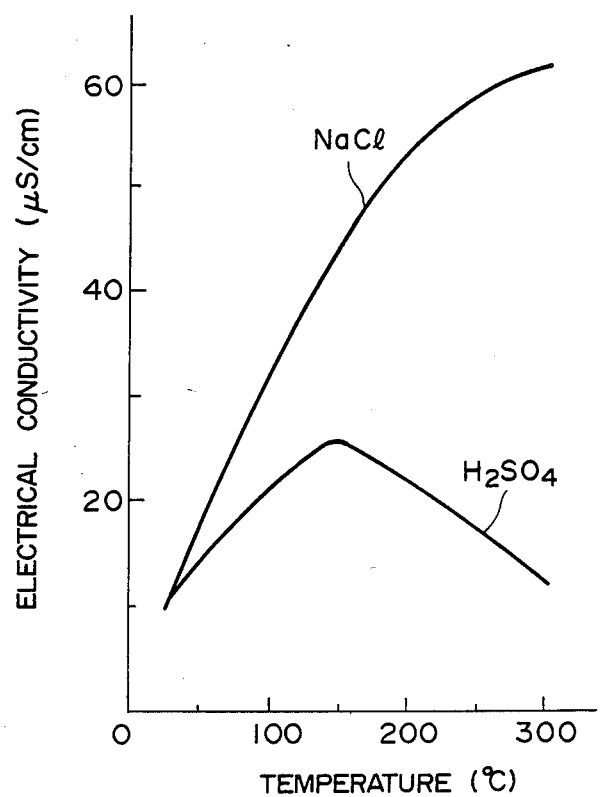
FIG. 21 is a graph showing a comparison between an aqueous NaCl solution and an aqueous $H_2SO_4$ solution as to changes in electrical conductivities with temperature.

FIG. 21 shows a comparison between changes in electrical conductivity with temperature in both aqueous solutions (room temperature electrical conductivity of 10 $\mu$S/cm) of NaCl and H$_2$SO$_4$.

Figure 22:
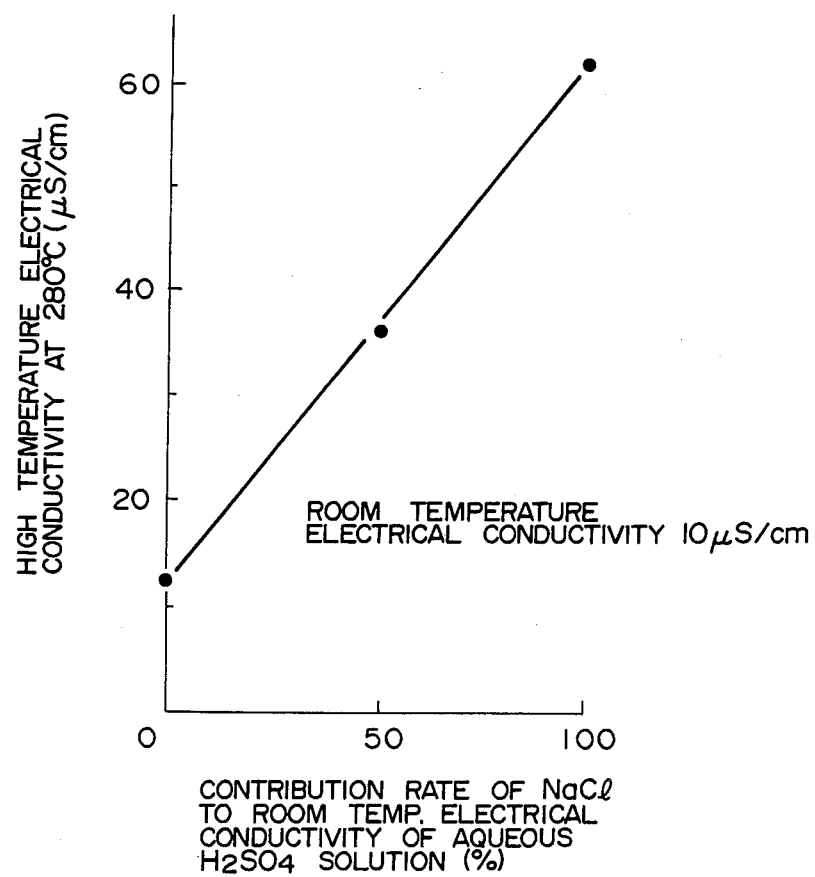
FIG. 22 is a graph showing a high temperature electrical conductivity of a mixed NaCl and $H_2SO_4$ solution at 280° C. as a function of a mixing ratio.

As shown in FIGS. 19 and 20, even when the room temperature electrical conductivity is the same, the high temperature electrical conductivities differ from each other depending on the chemical forms of the solute substances. In particular, when NaCl and H$_2$SO$_4$ are compared with each other, the difference between the high temperature electrical conductivities of both substances becomes significant in a high temperature region equal to 200° C. or higher in which H$_2$SO$_4$ does not dissociate completely. Thus, it is impossible to determine whether the solute substance is NaCl or H$_2$SO$_4$ by comparing a measured temperature dependency of electrical conductivity with the result shown in FIG. 21. In the embodiment, the chemical form of the impurity is determined by comparing the patterns of the temperature dependency of electrical conductivity with each other. However, it is possible to determine based on the amount of change in the electrical conductivity at two different temperatures. For example, by comparing the amount of change between a room temperature electrical conductivity and a high temperature electrical conductivity at 280° C. with the result shown in FIG. 21, it is possible to determine whether the impurity is NaCl or H$_2$SO$_4$. Furthermore, when NaCl and H$_2$SO$_4$ coexist, as shown in FIG. 22, the contribution rate of NaCl to the room temperature electrical conductivity increases, the value of the high temperature electrical conductivity at 280° C. increases from a value of an aqueous H$_2$SO$_4$ solution to a value of an aqueous NaCl solution substantially linearly. Accordingly, it is possible to quantitatively determine a mixing ratio of NaCl and $H_2SO_4$.

EMBODIMENT 5

Figure 23:
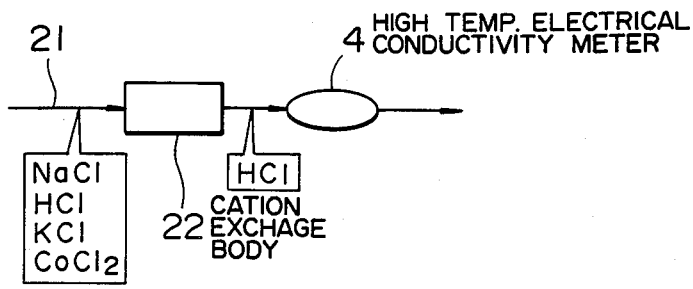
FIG. 23 is a diagram showing a modified example when the present invention is applied to high temperature water containing a plurality of chlorides.

When other chlorides are coexisting other than NaCl, as shown in FIG. 23 a heat-resisting cation exchange body 22 is provided at the upstream side of a high temperature electrical conductivity meter 4, and all the chlorides are converted in the form of HCl. Accordingly, the concentration of Cl ion can be determined quantitatively. For example, as the heat-resisting cation exchange body 22, iron oxide ($Fe_3O_4$) is used, and when high temperature water at 280° C. and including HCl, KCl, and $CoCl_2$ other than NaCl is fed through a column filled with the iron oxide, the $Na^+$, $K^+$ and $Co_2^+$ ions are replaced by $H^+$ ions on the surface of the iron oxide. As a result, the cation component in the water in the outlet of the column includes only $H^+$ ion, and the anion component in the water includes only $Cl^-$ ion. Accordingly, the temperature dependency of electrical conductivity of the aqueous HCl solution is obtained in advance, and by comparing the temperature dependency in the aqueous HCl solution with the temperature dependency of electrical conductivity exhibited by the water in the outlet of the column, it is possible to decide the presence or absence of the Cl ion. Furthermore, the concentration of the Cl ion can be determined quantitatively from the electrical conductivity at room temperature at which HCl dissociates to ions completely.

EMBODIMENT 6

Figure 24:
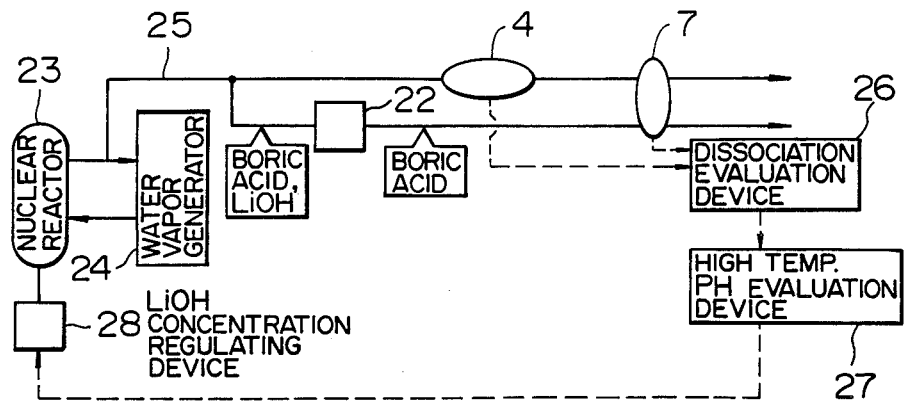
FIG. 24 is a schematic diagram showing a modified example when the present invention is applied to optimum control of high temperature pH in the PWR type nuclear reactor primary system.

FIG. 24 illustrates an embodiment in which the present invention is applied to optimum control of pH of high temperature water in a primary cooling system of a power water type atomic plant (hereinafter referred to as PWR). In FIG. 24, reference numeral 23 designates a nuclear reactor, 24 a water vapor generator, 25 a primary system high temperature water sampling line, 26 a dissociation evaluation device of boric acid, 27 a high temperature pH evaluation device, and 28 an LiOH concentration regulating device. In the high temperature water in the PWR primary system, the boric acid is added to control the degree of reaction. The concentration of the boric acid is lowered with the progress of operation of the plant. On the other hand, in order to suppress a decrease of pH due to the addition of the boric acid, LiOH is added, and the concentration of LiOH is controlled so that pH at high temperatures assumes an optimum value (around 7) from the standpoint of suppressing the corrosion. However, pH at the corrosive environment temperature is not directly measured, and the control is performed based on high temperature pH calculated from measured values of boric acid and LiOH concentrations, and based on high temperature pH calculated from the dissociation of an aqueous boric acid solution. However, generally, since the dissociation of electrolyte is influenced by solvent and other coexisting electrolytes, more accurate optimum control of high temperature pH is possible by using the extent of dissociation of boric acid in high temperature water in which LiOH and boric acid coexist.

In the present invention, in order to realize the two types of control method above, firstly, as shown in FIG. 24, a high temperature electrical conductivity in high temperature water at a corrosive environment temperature is measured. From the measured result, the extent of dissociation of boric acid at the corrosive environment temperature is determined. In other words, since LiOH dissociates to ions almost completely even in high temperature water, the electrical conductivity of high temperature water in which boric acid and LiOH coexist can be calculated as a function of the extent of dissociation of the boric acid. On the other hand, from the actually measured value of the high temperature electric conductivity, it is possible to determine the extent of dissociation of boric acid in a corrosive environment when LiOH coexists. In calculating the electrical conductivity mentioned above, although the concentrations of boric acid and LiOH are necessary, these concentrations can be obtained in the following manner from a measured value of the electrical conductivity in a temperature region in which boric acid dissociates almost completely, for example, at a room temperature. Specifically, by supplying high temperature water to a cation exchange body, the boric acid concentration can be obtained from a room temperature electrical conductivity of sampling water in which LiOH has been removed. Furthermore, the LiOH concentration can be obtained from a difference between a room temperature electrical conductivity of sampling water which is not supplied to the cation exchange body and a room temperature electrical conductivity of sampling water in which LiOH has been removed by passing through the cation exchange body. The concentrations of boric acid and LiOH obtained by in-line measurement of the electric conductivity in a temperature range from the corrosive environment temperature to the room temperature, and the extent of dissociation of boric acid at the corrosive environment temperature are used to calculate a concentration of hydrogen at the corrosive environment temperature, that is, high temperature pH is obtained. The calculated high temperature pH is compared with an optimum control value of high temperature pH to determine which is larger, and when pH is larger than the optimum control value, the LiOH concentration is reduced. Conversely, when pH is smaller than the optimum control value, the LiOH concentration is increased. In this manner, the LiOH concentration regulating device is controlled, and it is possible to maintain pH at an optimum value.

As described above, the in-line analysis of the concentrations of boric acid and LiOH can be achieved, and at the same time, the high temperature pH control which is accurate and quick in response, and which takes the extent of dissociation of boric acid at the corrosive environment temperature into consideration can be realized easily.

In the above embodiment, there is shown an example of application of the present invention to the evaluation of high temperature pH in a mixed aqueous solution of boric acid and LiOH. However, the present invention is not limited to such a combination but is generally applicable to the evaluation of high temperature pH in a mixed aqueous solution containing a plurality of electrolytes.

In the present invention, it is possible to perform the water quality control by accurately measuring the electrical conductivity of an aqueous solution even when the aqueous solution is in a relatively high temperature region equal to or higher than room temperature in which the solute substance does not dissociate completely.

Furthermore, by analyzing the corrosion rate and the concentration of corrosive anion by using an electrical conductivity measuring apparatus, it is possible to easily realize the water quality control which takes into consideration a difference in the influence on the corrosion due to a chemical form of a solute substance in high temperature water, in particular, in a temperature region in which the solute substance dissociates incompletely. In addition, since the water quality control standard value is set for each chemical form of the solute substances individually, it is possible to rationally moderate the water quality control standard value used at the present time which is excessively severe, without degrading the safety in the water quality control.

We claim:

1. A method of water quality control comprising the steps of:
    (a) measuring electrical conductivities of an aqueous solution under measurement at least at a temperature To and a temperature Tn, and obtaining a relationship between the electrical conductivity and the temperature, wherein the measurement temperature To is in a first range, and the measurement temperature Tn is in a second range different from said first range, and at least one value of the electrical conductivity is measured in each of the temperature ranges;
    (b) utilizing a determining means to determine a solute substance in said aqueous solution under measurement by applying the relationship obtained in said step (a) to a relationship between a temperature and an electrical conductivity of an individual substance obtained beforehand; and
    (c) utilizing an estimating means to estimate a concentration of the substance determined in said step (b) by applying the electrical conductivity at a lowest temperature To among the measurement temperatures in said first temperature range in said step (a) to a relationship between an electrical conductivity and a concentration at the same temperature To with respect to an individual substance obtained beforehand.

2. A method according to claim 1, wherein said first range is from a predetermined temperature up to 100° C., and said second range is from 150° to 280° C.

3. A method of measuring an electrical conductivity of an aqueous solution comprising the steps of:
    (A) immersing at least a pair of electrodes in said aqueous solution under measurement in order to obtain a relationship between an electrical conductivity and a temperature by measuring electrical conductivities at least at two different temperatures To and Tn with respect to said aqueous solution under measurement, and measuring a complex AC impedance between said pair of electrodes at each of the temperatures of said aqueous solution by applying an AC voltage between said pair of electrodes while varying a frequency of the AC voltage, wherein the measurement temperature To is in a first range, and the measurement temperature Tn is in a second range different from said first range, and at least one value of the electrical conductivity is measured in each of the temperature ranges;
    (B) obtaining a liquid resistance of said aqueous solution under measurement at each of the measurement temperatures from a frequency response of each of the complex impedance;
    (C) obtaining an electrical conductivity at each of the measurement temperatures from said liquid resistance;
    (D) determining a solute substance in said aqueous solution under measurement by applying a relationship between the measurement temperatures and the electrical conductivities to a relationship between a temperature and an electrical conductivity with respect to an individual substance; and
    (E) estimating a concentration of the solute substance determined in said step (D) by applying the relationship between a lowest temperature To in said first temperature range and the electrical conductivity obtained in said step (C) to a relationship between the same temperature To and a concentration with respect to an individual substance obtained beforehand 4. A method according to claim 3 wherein, in said steps (A) and (B), said liquid resistance is obtained by using a pair of electrodes, detecting a maximum value of absolute values of imaginary parts of said complex AC impedances between said pair of electrodes, obtaining an electrode surface reaction resistance value of said electrodes from the maximum value, and subtracting the maximum value of the absolute values of the imaginary parts from a real part of the complex AC impedance corresponding to said maximum value.

5. A method according to claim 3 wherein, in said steps (A) and (B), said liquid resistance is obtained by
    immersing two measuring electrode pairs X and Y into said aqueous solution, said two measuring electrode pairs X and Y respectively having electrode intervals different from each other and having substantially identical electrochemical, electrode surface reaction resistances,
    measuring the complex AC impedances between the electrodes of said electrode pair X by applying the AC voltage between said electrodes while changing a frequency thereof,
    measuring the complex AC impedances between the electrodes of said electrode pair Y by applying the AC voltage between said electrodes while changing a frequency thereof,
    detecting a minimum value of absolute values of imaginary parts of the complex AC impedances between the electrodes of said electrode pair X, said minimum value being in a frequency range close to a DC side of said AC voltage, and obtaining from said minimum value a combined resistance consisting of an electrode surface reaction resistance and a liquid resistance between the electrodes of said electrode pair X,
    detecting a minimum value of absolute values of imaginary parts of the complex AC impedances between the electrodes of said electrode pair Y, said minimum value being in a frequency range close to a DC side of said AC voltage, and obtaining from said minimum value a combined resistance consisting of an electrode surface reaction resistance and a liquid resistance between the electrodes of said electrode pair Y,
    obtaining the liquid resistance of said aqueous solution from a difference between the combined resistances of said electrode pair X and said electrode pair Y, and
    obtaining the electrical conductivity of said aqueous solution from said liquid resistance.

6. A method according to claim 5 wherein the applied frequencies are in a range of 10–100 Hz.

7. A method according to claim 3, wherein said first range is from a predetermined temperature up to 100° C., and said second range is from 150° to 280° C.

8. A method of water quality control for analyzing a corrosive substance in an aqueous solution with a metallic structural member dipped therein, and for detecting a corrosion rate of said metallic structural member, said method comprising the steps of:

(A) immersing at least a pair of electrodes in an aqueous solution under measurement in order to obtain a relationship between an electrical conductivity and a temperature by measuring electrical conductivities at least at two different temperatures To and Tn with respect to said aqueous solution under measurement, and measuring a complex AC impedance of said aqueous solution between said pair of electrodes at each of the measurement temperatures by applying an AC voltage between said pair of electrodes while varying a frequency thereof;

(B) obtaining a liquid resistance of said aqueous solution under measurement at each of the measurement temperatures from a frequency response of each complex AC impedance;

(C) obtaining an electrical conductivity at each of the measurement temperatures from said liquid resistance;

(D) deciding a corrosion rate of said metallic structural member in contact with said aqueous solution by applying a relationship between a maximum temperature in the measurement temperatures and the electrical conductivity to a relationship between an electrical conductivity and a corrosion rate of an individual substance obtained beforehand;

(E) determining a solute substance in said aqueous solution under measurement by applying the relationship between the measurement temperatures and the electrical conductivity to a relationship between a temperature and an electrical conductivity of an individual substance obtained beforehand; and (F) with respect to the determined substance, estimating a concentration of said substance by applying a part of the relationship obtained in said step (C), that is, the relationship between the temperature and the electrical conductivity at a lowest temperature To, to a relationship between an electrical conductivity and a concentration at the same temperature To with respect to an individual substance obtained beforehand.

9. A method according to claim 8 wherein, in said steps (A) and (B), said liquid resistance is obtained by using a pair of electrodes, detecting a maximum value of absolute values of imaginary parts of said complex AC impedances, obtaining an electrode surface reaction resistance value of said electrodes from the maximum value, and subtracting the maximum value of the absolute values of the imaginary parts from a real part of the complex AC impedance corresponding to said maximum value.

10. A method according to claim 8 wherein, in said steps (A) and (B), said liquid resistance is obtained by immersing two measuring electrode pairs X and Y into said aqueous solution, said two measuring electrode pairs X and Y respectively having electrode intervals different from each other and having substantially identical electrode surface reaction resistances, measuring the complex AC impedances between the electrodes of said electrode pair X by applying the AC voltage while changing the frequency thereof, measuring the complex AC impedances between the electrodes of said electrode pair Y by applying the AC voltage while changing the frequency thereof, detecting a minimum value of absolute values of imaginary parts of the complex AC impedances between said electrode pair X, said minimum value being in a frequency range close to a DC side of said AC voltage, and obtaining from said minimum value a combined resistance consisting of an electrode surface reaction resistance and a liquid resistance between the electrodes of said electrode pair X, detecting a minimum value of absolute values of imaginary parts of the complex AC impedances between said electrode pair Y, said minimum value being in a frequency range close to a DC side of said AC voltage, and obtaining from said minimum value a combined resistance consisting of an electrode surface reaction resistance and a liquid resistance between the electrodes of said electrode pair Y, obtaining the liquid resistance of aid aqueous solution from a difference between the combined resistances of said electrode pair X and said electrode pair Y, and obtaining the electrical conductivity of said aqueous solution from said liquid resistance.

11. A method according to claim 10 wherein the applied frequency are in a range of 10–100 Hz.

12. A method according to claim 8, wherein To is in a range from a predetermined temperature up to 100° C., and Tn is in a second range from 150° to 280° C.

13. An apparatus for measuring an electrical conductivity of an aqueous solution by applying an AC voltage between measuring electrodes which are dipped in said aqueous solution containing ions, and measuring at least one of an electrode surface reaction resistance and a liquid resistance of said aqueous solution, said apparatus comprising:

a plurality of electrode pairs having respective electrode intervals different from each other and having substantially identical electrochemical, electrode surface reaction resistances;

means for measuring AC complex impedances between the electrodes of each said electrode pair by applying the AC voltage between said electrodes while changing a frequency thereof:

means for detecting a minimum value of absolute values of imaginary parts of the complex AC impedances between the electrodes of each said electrode pair, said minimum value being in a frequency range close to a DC side of said AC voltage, and for obtaining from said minimum value a combined resistance consisting of an electrode surface reaction resistance and a liquid resistance between the electrodes of each said electrode pair;

first means for obtaining the liquid resistance of said aqueous solution from a difference between the combined resistances of each said electrode pair; and second means for obtaining the electrical conductivity of said aqueous solution from said liquid resistance.

14. A method of water quality control for analyzing a corrosive substance in an aqueous solution with a metallic structural member dipped therein, and for detecting a corrosion rate of said metallic structural member, said method comprising the steps of:

(A) immersing at least a pair of electrodes in said aqueous solution under measurement in order to obtain a relationship between an electrical conductivity and a temperature by measuring electrical conductivities at least at a temperature To in a first range and a temperature Tn in a second range different from said first range with respect to said aqueous solution between said pair of electrodes at each of the measurement temperatures by applying an AC voltage between said pair of electrodes while varying a frequency thereof;

(B) obtaining a liquid resistance of said aqueous solution under measurement at each of the measurement temperatures from a frequency response of each of the complex AC impedances, wherein said liquid resistance is obtained by, immersing two measuring electrode pairs X and Y into said aqueous solution, said two measuring electrode pairs X and Y respectively having electrode intervals different from each other and having substantially identical electrochemical, electrode surface reaction resistances, measuring the complex AC impedances between the electrodes of said electrode pair X by applying the AC voltage between said electrode while changing a frequency thereof, measuring the complex AC impedances between the electrodes of said electrode pair Y by applying the AC votlage between said electrodes while changing a frequency thereof, detecting a minimum value of absolute values of imaginary parts of the complex AC impedances between the electrodes of said electrode pair X, said minimum value being in a frequency range close to a DC side of said AC voltage, and obtaining from said minimum value a combined resistance consisting of an electrode surface reaction resistance and a liquid resistance between the electrodes of said electrode pair X, detecting a minimum value of absolute values of imaginary parts of the complex AC impedances between the electrodes of said electrode pair Y, said minimum value being in a frequency range close to a DC side of said AC voltage, and obtaining from said minimum value a combined resistance consisting of an electrode surface reaction resistance and a liquid resistance between the electrodes of said electrode pair Y, obtaining the liquid resistance of said aqueous solution from a difference between the combined resistances of said electrode pair X and said electrode pair Y, and obtaining the electrical conductivity of said aqueous solution from said liquid resistance;

(C) obtaining an electrical conductivity at each of the measurement temperatures from said liquid resistance;

(D) deciding a corrosion rate of said metallic structural member in contact with said aqueous solution by applying a relationship between a maximum temperature in the measurement temperatures and the electrical conductivity to a relationship between an electrical conductivity and a corrosion rate of an individual substance obtained beforehand;

(E) determining a solute substance in said aqueous solution under measurement by applying the relationship between the measurement temperature and the electrical conductivity to a relationship between a temperature and an electrical conductivity of an individual substance obtained beforehand; and (F) with respect to the determined substance, estimating a concentration of said substance by applying a part of the relationship obtained in said step (C), that is, the relationship between the temperature and the electrical conductivity at a lowest temperature To, to a relationship between an electrical conductivity and a concentration at the same temperature To with respect to an individual substance obtained beforehand.

15. A method according to claim 14, wherein said first range is from a predetermined temperature up to 100° C., and said second range is from 150° to 280° C.

* * * * *